United States Patent
Van Dyck et al.

(10) Patent No.: US 8,399,230 B2
(45) Date of Patent: Mar. 19, 2013

(54) HEAT-STABLE ENZYME COMPOSITIONS

(75) Inventors: Stefaan M. O. Van Dyck, Brasschaat (BE); Bruno Coppens, Heist-op-den-berg (BE); Ingrid Somers, Kasterlee (BE); Clifford A. Adams, Berchem (BE)

(73) Assignee: Kemin Industries, Inc., Des Moines, IA (US)

( * ) Notice: Subject to any disclaimer, the term of this patent is extended or adjusted under 35 U.S.C. 154(b) by 0 days.

(21) Appl. No.: 11/546,859

(22) Filed: Oct. 12, 2006

(65) Prior Publication Data

US 2008/0090276 A1 Apr. 17, 2008

(51) Int. Cl.
*C12N 11/04* (2006.01)

(52) U.S. Cl. ........................................................ 435/182

(58) Field of Classification Search .................. None
See application file for complete search history.

(56) References Cited

U.S. PATENT DOCUMENTS

| | | | |
|---|---|---|---|
| 4,891,319 A | 1/1990 | Roser | |
| 5,318,903 A | 6/1994 | Bewert et al. | |
| 5,391,371 A | 2/1995 | Jacobsen et al. | |
| 5,624,831 A | 4/1997 | Khue et al. | |
| 5,827,709 A * | 10/1998 | Barendse et al. | 435/188 |
| 5,876,992 A | 3/1999 | De Rosier et al. | |
| 6,136,772 A | 10/2000 | De Lima et al. | |
| 6,500,426 B1 | 12/2002 | Barendse et al. | |
| 6,541,606 B2 | 4/2003 | Margolin et al. | |
| 6,602,843 B2 | 8/2003 | Markussen | |
| 6,841,168 B1 | 1/2005 | Worrall | |
| 7,186,533 B2 * | 3/2007 | Andela et al. | 435/183 |
| 2002/0102329 A1* | 8/2002 | Lanahan et al. | 426/46 |
| 2003/0049811 A1 | 3/2003 | Barendse et al. | |
| 2003/0054511 A1 | 3/2003 | Andela et al. | |
| 2004/0241208 A1* | 12/2004 | Sowden et al. | 424/440 |
| 2005/0175602 A1* | 8/2005 | Cook et al. | 424/130.1 |

FOREIGN PATENT DOCUMENTS

| | | |
|---|---|---|
| EP | 0501375 A1 | 9/1992 |
| EP | 1069832 B1 * | 5/2004 |
| WO | WO 00/47060 | 8/2000 |
| WO | WO 03/026616 A1 | 4/2003 |

OTHER PUBLICATIONS

Cardona et al., Journal of Food Science, vol. 62, No. 1, p. 105-112.*
DePaz et al., Enzyme and Microbial Technology, 2002, vol. 31, p. 765-774.*
Liao et al., Pharmaceutical Research, 2002 vol. 19, No. 12, p. 1847-1853.*
Terebiznik et al., Lebensm.-Wiss, u., Technol., 1997, vol. 30, p. 513-518.*
Kirkpinar et al., Czech J. Anim. Sci., Feb. 2006, vol. 51, No. 2, p. 78-84.*
Drusch et al., Food Research International, Mar. 2006, vol. 39, p. 807-815.*
Cardona et al., Journal of Food Science, 1997, vol. 62, No. 1, p. 105-112.*
Colaco, et al., *Chemistry of Protein Stabilization by Trehalose*, Formulation and Delivery of Proteins and Peptides, 1994, American Chemical Society. p. 222-240.
Jennifer Kovacs-Nolan and Yoshinori Mine, Passive Immunization Through Avian Egg Antibodies, Food Biotechnology, vol. 18, No. 1, pp. 39-62, 2004, Canada.
M. Ellin Doyle, Ph.D., Alternatives to Antibiotic Use for Growth Promotion in Animal Husbandry, Food Research Institute, University of Wisconsin-Madison, pp. 1-17, Apr. 2001.
Cardona S et al: "Thermal Stability of Invertase in Reduced-Moisture Amorphous Matrices in Relation to Glassy State and Trehalose Crystallization" Journal of Food Science, Wiley-Blackwell Publishing, Inc, US LNKD-DOI:10.1111/J.1365-2621.1997.TBO4378.X, vol. 62, No. 1, Jan. 1, 1997, pp. 105-112, XP001194580, ISSN: 0022-1147.
Depaz R A et al: "Effects of Drying Methods and Additives on the Structure, Function, and Storage Stability of Subtilisin; Role of Protein Conformation and Molecular Mobility" Enzyme and Microbial Technology, Stoneham, MA US LNKD—DOI:10.1016/S0141-0229(02)00173-4,vol. 31, No. 6, Nov. 1, 2002, pp. 765-774, XP001179325 ISSN: 0141-0229.
Cui L et al: "Stabilization of a new microbial transglutaminase from *Streptomyces hygroscopius* WSH03-13 by spray drying" Process Bichemistry, Elsevier, NL LNKD—DOI:10.1016/J.PROCBI0.2006.01.002, vol. 41, No. 6, Jun. 1, 2006, pp. 1427-1431, XP025124804 ISSN: 1359-5113.
Liao et al. Effects of Sucrose and Trehalose on the Preservation of the Native Structure of Spray-dried lysozyme, Pharmaceutical Research, Dec. 2002, vol. 19, p. 1847-1853. p. 1847 1st column 2nd paragraph, 2nd column lines 1-8, p. 1849 1st column 1st paragraph, and 2nd column 2nd paragraph, lines—13, p. 1847 2nd column 2nd paragraph lines 24-28.

* cited by examiner

*Primary Examiner* — Kade Ariani

(74) *Attorney, Agent, or Firm* — Davis, Brown, Koehn, Shors & Roberts, P.C.; Kent A. Herink

(57) ABSTRACT

The thermal stability of enzymes is improved by incorporating the enzyme in a matrix of a non-reducing sugar, such as trehalose. Heat-stable compositions of enzymes and sugar are formed by adding the enzymes to a sugar syrup and drying the mixture either by spreading it on a carrier or by spray drying. The enzyme compositions retain higher levels of activity after being subjected to heat in product-forming processes, such as steam pelleting of animal feed supplemented with the enzyme compositions.

18 Claims, 1 Drawing Sheet

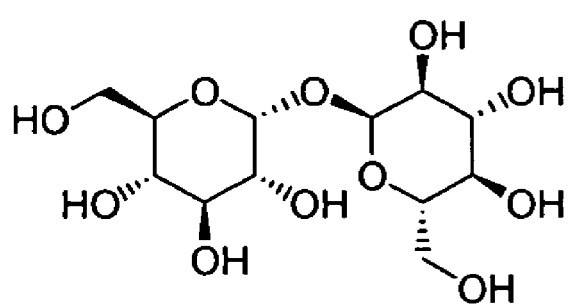 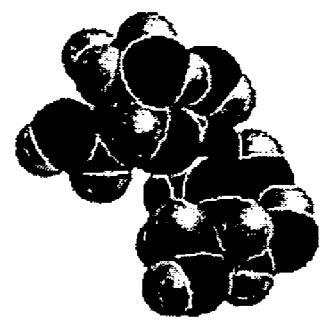

HEAT-STABLE ENZYME COMPOSITIONS

BACKGROUND OF THE INVENTION

The present invention relates generally to heat- or thermostable enzymes and, more specifically, to enzymes that have been protected by a non-reducing saccharide, for example, trehalose, to improve their heat stability during feed processing. The enzyme compositions have an increased stability during steam treatment due to the presence of the saccharide and can be used in animal feed or food composition that are steam treated.

The potential commercial application of enzymes for maximizing animal performance through the improvement of nutrient digestion is significant. Unfortunately, the main obstacle for the full development of this market is the observation that a variety of enzymes are intrinsically unstable. This instability becomes apparent in two main areas. First, enzymes may lose activity during storage before use. This issue can be partially managed by strict control of the storage conditions. More significant is the loss of activity during the various processing conditions in animal feed production. Certainly under pelleting conditions many enzymes are inactivated. Although feed pelleting represents a cost in terms of energy, it provides several benefits. It is well known that pelleting increases the digestibility of the starch fraction. Besides the higher bioavailability of some nutrients there is also less feed waste, a more uniform nutrition and improved feed handling because of reduced dustiness. Pelleting also becomes more important in the context of food safety. Most microorganisms are sensitive to heat under conditions of high moisture. Therefore the feed industry increasingly uses steam pelleting in order to reduce the microbiological load of the feed.

Pelleting also becomes more important in the context of food safety. Feed crises during recent years have had enormous consequences causing a decrease of consumer confidence in the feed industry. Today, consumers only want safe food products. The modern feed industry must now establish procedures and practices in order to manage the risks associated with their activity. The major hazards in feed can only be controlled by strict application of HACCP and GMP as critical and basic food safety management systems.

There has been much emphasis upon Salmonella control in recent years and it is now well recognized that raw materials and feeds can be readily contaminated by *Salmonella*. Another concern with *Salmonella* today is the prevalence of strains with multiple antibiotic resistances. In recent years, both in Europe and the United States, the presence of *Salmonella typhimurium* DT 104 has been reported, initially in cattle, but now spreading to other species and this serotype has multiple resistance to many antibiotics. Control of *Salmonella* in pig production to reduce *Salmonella* contamination in pig carcasses is also an important food safety concern.

Programs for the control of *Salmonella* and other pathogens in raw materials and feeds usually require either heat processing or chemical treatment with bacterial inhibitors. A combination of heat and chemical processing is also sometimes used, particularly in manufacturing critical feeds such as those for high-value poultry breeding stock.

*Salmonella* are sensitive to heat under conditions of high moisture and an example is pasteurizing milk where heating at 70° C. or above for 15 seconds is sufficient to destroy *Salmonella*. However, in the animal production industries it is important to appreciate that raw materials and animal feeds are basically dry materials with a moisture content usually below 14-15%. *Salmonella* are resistant to drying and become more heat resistant as they dehydrate. *Salmonella* may survive on surfaces and in dust for years. Davie and Wray (Persistence of *Salmonella Enteritidis* in poultry units and poultry feed, British Poultry Science 37, 589-596 (1996)) showed that *S. Enteritidis* and other serotypes persisted in poultry feed for at least ten months. Therefore feed production increasingly makes use of steam pelleting in order to reduce the microbiological load of the feed.

The supplementation of diets with enzymes in order to improve the digestibility of animal feeds is an established practice since more than a decade, Unfortunately the harsh conditions that destroy microorganisms are also detrimental to enzymes. The increasing application of heat treatment of feeds poses a significant challenge for the development and use of enzyme feed supplements. Enzymes are complex protein structures that obtain their typical activity from their amino acid composition together with their three-dimensional structure. It is generally known that most enzymes are susceptible to heat treatment processes. In the pelleting process, feed is first subjected to a conditioner phase to prepare the feed for being pressed into pellets. In the conditioner, direct stream addition takes place and the average moisture content of feed increases. Steam addition also results in an increase of the temperature up to 60-95° C. The combination of a high environmental temperature and the presence of water for a certain time period cause enzyme denaturation. The enzymes will often irreversibly loose their conformation and consequently also their enzymatic activity. A solution to this problem, which has been applied for many years, is to apply enzymes after the pelleting process by spraying enzymes in the form of liquid solutions onto the pellets after they are cooled.

The improvement of heat stability is an important challenge in the context of enzyme development for the animal feed industry. It is known that enzymes can be stabilized by encapsulation in a protecting matrix. The loss of enzyme activity may be overcome by "immobilization" or "encapsulation" of enzymes (Faber, K. Biotransformations in Organic Chemistry, 4th ed.; Springer, Berlin (2000)). These techniques involve either the attachment of an enzyme to a solid support (coupling onto a carrier) or linkage of the enzyme molecules to each other (cross-linking). Alternatively the biocatalyst may be confined to a restricted area from which it cannot leave but where it remains catalytically active (entrapment into a solid matrix or a membrane restricted compartment). As a consequence, homogeneous catalysis using a native enzyme often turns into heterogeneous catalysis when immobilized enzymes are employed.

The use of immobilized enzymes in animal feed adds another level of complexity to this subject matter. Strict heterogeneous catalysis would imply that the enzyme is not soluble anymore and cannot be separated from a feed sample with simple extraction techniques. This phenomenon will pose serious difficulties for the recovery of the enzyme activity in the feed. It will be impossible to measure enzyme activities, which is a strict requirement for registration. It is possible to circumvent this issue by using a water-soluble matrix. Optimally this matrix will remain intact during the pelleting, but should dissolve easily in the digestive tract in order to liberate the enzymes (Gray, C. J. Thermostability of Enzymes, ed: M. N. Gupta, Springer, Berlin (1993)).

SUMMARY OF THE INVENTION

The present invention consists of compositions of one or more enzymes and a non-reducing sugar, preferably trehalose, which provides enhanced thermal stability to the enzymes by encapsulating the enzymes in a sugar matrix so that the activity of the enzymes is maintained at a high level through processing operations that subject the enzyme compositions to heat.

Two different processes can be used to produce the protected enzyme products. The first process starts with a syrup of the sugar which is combined with an enzyme solution and the mixture is then absorbed on an inert carrier in order to obtain a dry product. The second process starts with a more dilute solution of the combined sugar and enzyme, which is spray dried to obtain a dry product. Both processes generate very good recoveries of the activities of two different enzymes, a protease and a xylanase, in the novel products. In particular, a strong increase of the activity of xylanase protected using the spray-drying process was observed. More units of activity were recovered in the spray-dried product compared to the initial activity level in the unprotected starting material, while taking into account dilution factors. Also, the stability of the encapsulated enzymes during a laboratory scale steam treatment of feed was studied. For protease, a very strong residual activity of 80% after steam treatment was observed for the novel product obtained via the syrup process, and 67% for the spray-dried product. For xylanase, only the syrup process yielded a product with sufficient thermostability.

A purpose of the present invention is to provide enzyme products having improved resistance to loss of activity during processing under heated conditions.

Another purpose of the invention is to provide enzyme products for addition to animal feeds that retain high levels of activity after pelleting, including steam pelleting.

A further purpose of the present invention is to provide enzymes protected against loss of activity during heat processing which retain a high level of activity in a target organism.

Another purpose of the present invention is to provide enzymes protected against loss of activity during storage at varying warehouse temperatures.

These and other objects of the invention will be made apparent to those skilled in the art upon a review of this specification, the associated drawings and the appended claims.

BRIEF DESCRIPTION OF THE DRAWINGS

FIG. 1 is a structural formula and three-dimensional representation of trehalose.

DETAILED DESCRIPTION OF PREFERRED EMBODIMENTS

The present invention provides an enzyme composition including an enzyme-containing starting material that is suitable for use in animal feed which will be decontaminated from microorganisms using steam with or without additional heat treatment or other kinds of heat processing. Enzyme-containing starting materials stabilized by processes of the present invention will remain stable in the final enzyme composition after heat treatment or heat processing. An enzyme composition is stable, remains stable or has enhanced thermal stability if after heat treatment or heat processing the activity of a stabilized enzyme composition is reduced by less than the reduction of the same enzyme-containing starting materials not stabilized under the processes of the present invention. Preferably, the loss in activity of a stabilized enzyme composition is 10% less than that of the same enzyme-containing starting materials not stabilized under the processes of the present invention. More preferably, the loss in activity of a stabilized enzyme composition is 25% less than that of the same enzyme-containing starting materials not stabilized under the processes of the present invention. Most preferably, the loss in activity of a stabilized enzyme composition is 50% less than that of the same enzyme-containing starting materials not stabilized under the processes of the present invention. Activity can be measured by any means known in the art, including measurement of the nitrogen released into the aqueous phase after incubation, the use of Nelson's reagent, or commercially available assay materials and kits. Enzyme-containing starting materials are not limited to a purified protein fraction, but include fermentation products, such as fermentation liquid fractions, liquid commercial enzyme products containing additional solvents or stabilizers, and dry enzyme products which have had water removed, for example by spray-drying or absorption on a carrier.

The enzyme powders are produced from a liquid premix comprising at least a non-reducing sugar and at least one single fermentation enzyme product. Other ingredients in the premix can be, but are not restricted to water, polyols, salts, surfactants, carrier materials and enzyme stabilizing compounds in general. The non-reducing sugar can be a disaccharide or an oligosaccharide. The saccharide is chosen from the group of non-reducing disaccharides and oligosaccharides. Non-reducing sugars are those sugars that do not contain a hemiacetal. Non-reducing sugars include sucrose, trehalose, sorbose, melezitose, verbascose, melibiose, sucralose and raffinose. Most preferred are the non-reducing disaccharides sucrose and trehalose.

In a preferred embodiment a saccharide is first dissolved in water. In a second step the mixture is heated and the water is evaporated until a syrup with a low water content is obtained. A liquid enzyme is added to the hot syrup after which the mixture is put on a carrier.

In an alternative procedure the saccharide is dissolved in water and the enzymes are added. Also a carrier material can be added. Preferred carriers include limestone, vermiculite, silica, cyclodextrin, maltodextrin, gelatin, cornstarch, sepiolite, bentonite, zeolite and cellulose. A dry powder can be obtained either by drying, for example, spray drying, or by combining the product with a carrier.

The enzyme ingredients that are used in the process can be either liquid or solid or both. Solid enzymes are dissolved first in a minimal amount of water or polyalcohol (e.g. monopropylene glycol, glycerol) before they are combined with the saccharide premix.

Commercial enzyme formulations can be used to prepare the saccharide premix. Enzyme formulations with the highest activity are preferred in order to avoid a possible destabilizing effect of other ingredients present in the formulation. Liquid enzymes are often more diluted and contain higher boiling polyalcohols such as mono propylene glycol, which are not removed completely during the process and therefore require higher amounts of carrier in order to obtain a free-flowing powder.

The preferred enzymes to be used in feed have a pH optimum close to neutral pH and a temperature optimum close to the animal's body temperature. Possible enzymes comprise hydrolases and, more specifically, proteases such as Neutrase 0.8 L or 1.5 MG (Novozymes), having optimal working conditions that are at 45-55° C. (113-131° F.) and pH 5.5-7.5, alpha-amylases (for example, Termamyl 120 L, Novozymes), cellulases (for example, Celluclast 1.5 L, Novozymes), xylanases (for example, Ronozyme WX, DSM)), beta-glucanases (for example, Econase BG 300, AB Enzymes), alpha-galactosidases (for example, Galactomax Liquid, Kemin Consumer Care), and alpha-amylases combined with beta-glucanases (for example, BAN 480 L, Novozymes).

The saccharide syrup is prepared by mixing the saccharide in a 1 to 1 up to 1 to 10 ratio with water at 100° C. When the saccharide is fully dissolved, at least some of the water is evaporated by additional heating. In this way solutions can are prepared which are above their saturation point at room temperature. The residual amount of remaining water is in between 20% and 0.01% and most preferred in between 3% and 0.05%.

The saccharide is chosen from the group of non-reducing disaccharides and oligosaccharides. Non-reducing sugars are those sugars that do not contain a hemiacetal. Non-reducing sugars include sucrose, trehalose, sorbose, melezitose, verbascose, melibiose, sucralose and raffinose. Most preferred are the disaccharides sucrose and trehalose.

Immediately after the preparation of the saccharide syrup the enzymes are added. The syrup is not cooled down first because this may cause the carbohydrates to crystallize in concentrated syrups. Liquid enzymes can be used as such while solid enzyme products are first dissolved in water or another polar solvent such as a polyalcohol. The amount of solvent is chosen to dissolve all of the enzyme. A minimal amount of solvent is used to allow solution of the enzyme while maintaining an acceptable viscosity. Preferably an enzymatic activity between 5,000 and 10,000,000 units is present in one gram of solubilized enzyme or commercial liquid enzyme formulation. Most preferred is an enzyme activity between 10,000 and 5,000,000 units.

The solubilized enzyme or commercial enzyme formulation is mixed with the saccharide syrup in order to obtain a mixture containing in between 1% and 75% of the liquid enzyme formulation and in between 99%-10% of saccharide. Preferably the enzyme concentration is in between 10% and 60% and the saccharide concentration between 90% and 40%.

The temperature of the disaccharide syrup prior to mixing with the liquid enzyme is between 50° C. and 130° C. and most preferably between 80° C. and 110° C.

Immediately after the production of the enzyme-saccharide syrup, the entire mixture may be absorbed on a carrier. Long waiting times may result in partial recrystallisation of the saccharide. Suitable carriers are for example, but not limited to: silica gel, clay materials, calcium carbonate, almond shell meal, chicory fiber fraction and rice bran.

The preferred ratio of the enzyme-saccharide syrup and carrier depend on the type of carrier. The ratio is determined by the absorption characteristics of the carrier. An amount of carrier is selected in order to obtain a dry powder. Typically the final product contains between 5 and 65% of enzyme-saccharide syrup and 35-95% carrier. In a preferred embodiment the final product contains between 20,000 and 2,400,000 units of enzyme activity.

Trehalose (FIG. 1) is a naturally occurring, non-reducing disaccharide composed of two D-glucopyranose units in α,α (1→1) linkage, and possesses particularly interesting physicochemical and biological properties. These features include two melting points, a highly stable α-linkage, an unusually high degree of optical rotation, and an extraordinarily high hydrated volume when compared with other disaccharides. Trehalose is well known as a stress protectant in several organisms. It accumulates as a physiological response to several conditions such as heat shock, desiccation, osmotic shock, and freezing (Higashiyama, T. Novel functions and applications of trehalose, Pure. Appl. Chem. 74: 1263-1269 (2002)).

Trehalose remains solid at temperatures used in pelleting, but advantageously dissolves relatively easy in water.

Trehalose dihydrate has a melting point of 97° C. When the free water in a trehalose solution is evaporated at ~100° C. the trehalose dihydrate will be present at that temperature in the liquid, molten state. When heating is then continued, the trehalose will start to lose its crystal water at ~130° C. Because the trehalose anhydrate only melts at 203° C. the product will solidify instantaneously when dehydrated.

Stabilized enzyme compositions of the present invention will have improved activity after heat processing than unstabilized enzyme compositions. Food and feed products containing enzymes are commonly subjected to heat processing which subject the products to elevated temperatures for varying periods of time, typically temperatures of between 50° C. and about 200° C. for between 1 second and up to several hours, depending on the process. Heat processing includes canning, sterilization, pasteurization, and pelleting. Stabilized enzyme compositions of the present invention with enhanced thermal stability have higher activity than non-stabilized enzyme compositions after heat processing under time and temperature conditions familiar to those skilled in the art. In general, the lower the temperature, the longer amount of time the product can be exposed to that temperature and remain stable and the higher the temperature, the shorter the amount of time the product can be exposed to that temperature and remain stable. Due to thermal lag, temperatures much higher than ordinary degradation temperatures can be withstood for short periods of time. Stabilized enzyme compositions of the present invention with enhanced thermal stability have higher activity than non-stabilized enzyme compositions after heat processing, from about 70° C. and about 90° C. for between about 25 seconds and about 10 minutes, at up to 100° C. for up to 5 minutes.

Example 1

General Procedure for the Preparation of an Enzyme/Trehalose Syrup

A total of 20 g trehalose dihydrate was dissolved in a beaker containing 20 g of in water that had been filtered using a Millipore Milli-Q® water purification system. The water was previously heated to in between 50 and 100° C. in order to accelerate dissolving. The beaker was tared and then heated on a heating plate equipped with a magnetic stirrer. The heater was set at 200° C. and the water evaporated, while the mixture was gently stirred. The amount of water evaporated was checked by weighing. When 95-97.5% of the water was evaporated the heating was stopped and 20 g of the commercial enzyme Neutrase® 0.8 L (Novozymes, Denmark) was slowly added to the trehalose syrup while stirring. Typically the temperature of the solution will drop from ~99° C. to ~65° C. The mixture was cooled down in a cold-water bath to achieve a mixture temperature below 35° C. The enzyme/trehalose syrup was then ready for further use and is preferably processed immediately. After one hour, the trehalose present in the formulation may start to crystallize. A solid product can be easily obtained by addition of the syrup to a suitable carrier, limestone, vermiculite, silica, cyclodextrin, maltodextrin, gelatin, cornstarch, sepiolite, bentonite, zeolite and cellulose.

Example 2

General Procedure for the Preparation of an Enzyme Encapsulated in Trehalose by Spray-Drying In a beaker, 50 g of water that had been filtered using a Millipore Milli-Q® water purification system was heated to 100° C. and 50 g of trehalose was added while stirring. No further heating was required. When the trehalose was dissolved, 6 g the enzyme mixture used in Example 1 was added. Also free flowing agents, such as vermiculite, silica, cyclodextrin, maltodextrin, gelatin, cornstarch, sepiolite and cellulose, can be added to the mixture. The liquid was spray dried using parameters that yield a dry free flowing powder These parameters include adjusting spray drying inlet and outlet temperatures and/or the addition of other amounts of the free flowing agent.

Example 3

General Procedure for the Steam Challenge Experiment

A Büchi distillation unit B342, typically used for Kjeldahl analysis was used as a steam generator for the steam challenge experiment. The outlet of the steam generation tube was connected with a rubber tube to the side neck of a double-necked flask. A glass Büchner filter was connected to the vertical neck of the flask by means of a rubber stopper. All elements were securely fastened with clamps because over-pressure is generated during the experiment. The steam produced by the distillation unit will enter the flask and the steam will partially condensate. The remaining vapors will mount through the vertical neck into the Büchner filter which is filled with a control matrix or an enzyme treated matrix. A homogeneous steam treatment is obtained by continuous stirring of the matrix.

A quantity of 1000 g of a typical broiler feed was supplemented with the enzyme to be tested at a dose rate of 1 kg/tonne. The feed was homogenized vigorously by transferring it into a plastic container and shaking. Aliquots of 50 g were transferred into a Büchner funnel and steam was allowed to pass through the sample via the bottom of the funnel. The steam was provided by a steam generator present in the distillation unit of a Kjeldahl system (B-324, Büchi, Switzerland). Steam treatment was applied for 30 seconds, which results in an increase of the temperature of the feed to about 80° C. and an increase of moisture content of about 5%. During steam passage, the feed was stirred manually using a spatula. After the treatment the sample was spread as a thin layer on an aluminum tray for 30 min.

When the apparatus was used for the first time the glassware was first preheated by passing 100% steam for two minutes through the system. Afterwards every sample was steamed according to the sequence below in order to guarantee the reproducibility of the steam challenge: (1) Condensed water was removed from the flask; (2) the glass ware is preheated for 50 s with 30% steam; (3) residual dust and moisture is removed from the Büchner filter with paper tissue; (4) the glass ware is preheated again for 50 s with 30% steam; (5) a third 50 s sequence with 30% steam is started and after 25 s a 50 g feed sample is poured into the Büchner filter and continuously stirred with a spatula while steam was passing through for 25 s; (5) the filter is removed immediately and emptied onto an aluminum tray. The feed was spread out to allow efficient cooling.

Example 4

General Procedure for Assessment of Protease Activity

Enzyme survival after steam treatment was determined relative to a standard series of feed samples which were not treated but also contained the stabilized enzyme.

The aim of the assay is to assess the residual protease activity of different enzyme formulations after these were dosed into to feed and challenged with a steam treatment. Protease activity is determined by measurement of the nitrogen released into the aqueous phase after incubation of the feed sample for 3 h at 40° C. Afterwards, the nitrogen content of the sample is determined, e.g., by Kjeldahl analysis.

Example 5

General Procedure for Assessment of Xylanase Activity

The determination of the recovery of xylanase was performed using Xylazyme AX tablets (Megazyme, Wicklow, Ireland). To improve the extraction efficiency a surfactant (Tween 20) was added during the extraction.

Results and Discussion

Protease Stabilisation Via the Syrup Process

Trehalose syrup was prepared as described in Example 1. The liquid commercial enzyme Neutrase 0.8 L was used as the protease source. A total of 10 g of the protease/trehalose syrup was absorbed on 10 g of silica (Sipemat 22S) in order to obtain a dry powder.

The enzyme activity after the syrup process was checked using Azo-casein (Cat. No.: S-AZCAS, Megazyme). Two samples were analyzed in duplicate and 99.7% and 106.1% of the enzyme activity was recovered indicating that protease easily withstands the syrup process.

Four groups of samples were then tested in a steam challenge: (1) Control group: steam treated, no enzyme added; (2) positive control: steam treated feed, protected enzyme added after heating; (3) negative control: unprotected enzyme added to the feed, mixture steam treated; and (4) experimental group: encapsulated enzyme added to the feed, mixture steam treated.

Enzyme activities in groups 1-3 were analysed in triplicate (three samples taken after one steam treatment). For group four a total of six analyses were performed (2×3 samples from two individual steam treatments). The results are represented in Table 1.

TABLE 1

Protease recovery in steam treated samples

| Group Number | Relative Protease Recovery (%) | Standard Deviation (%) |
|---|---|---|
| 1 | 0 | ±1.9 |
| 2 | 100 | ±3.7 |
| 3 | 0 | ±2.1 |
| 4 | 80.3 | ±4.2 |

Protease Stabilisation Via Spray Drying

A total of 3 g Neutrase 0.8 L was mixed with a syrup from 20 g trehalose and 25 g water and 5 g of an anti-caking agent, such as specified in Table 2, was added. This mixture was continuously stirred while it was spray dried.

Several mixtures with a variety of anti-caking agents were spray dried and the protease activity after the process and after steam treatment were measured as shown in Table 2.

TABLE 2

Protease recovery in spray dried samples

| Anti-caking Agent Used | Relative Protease Recovery in Product (%) | Relative Protease Recovery After Steam Challenge (%) |
|---|---|---|
| None | 116 | 65 |
| Corn stach (Melogel) | 98 | 67 |
| Sepiolite (Exal) | 75 | 64 |
| Gelatine (in 10 mL H$_2$O) | 104 | 44 |
| Dextrin | 111 | 54 |
| Cellulose | 101 | 70 |

The spray-dried product is somewhat less stable in the steam challenge compared to the product obtained via the syrup process. However, it should be noted that the spray drying system used were relatively rough and was not optimized. Under more controlled conditions a further improvement of the steam-stability can be expected.

The observed recovery values of >100% for the freshly spry-dried products are not unexpected. It is known from the literature that encapsulation potentially activates (renatures) enzyme activity (Zancan, P. and Sola-Penna, M. Trehalose and glycerol stabilize and renature yeast inorganic pyrophosphatase inactivated by very high temperatures, *Arch. Biochem. Biophys.* 444: 52-60 (2005)). The total recovered activity may therefore be higher compared to the starting material.

Xylanase Stabilisation Via the Syrup Process

A trehalose syrup was prepared as described in Example 1. The dry commercial enzyme Econase® HCP4000 (AS Enzymes, Germany) was used as the xylanase source. A total of 12.5 g of the enzyme was dissolved in 12.5 g water. This mixture was added to 25 g of the concentrated warm trehalose syrup and absorbed on 50 g of 40/60 limestone/silica.

The enzyme activity after the syrup process was checked using xylan from birchwood (Sigma, X-0502) as a substrate. One sample was analyzed in duplicate and 93.5% of the enzyme activity was recovered indicating that xylanase sufficiently withstands the syrup process.

TABLE 3

Xylanase recovered after addition of 40,000 u/g to a carrier system

| Carrier | Recovered Xylanase Activity (u/g) |
|---|---|
| Sipernat 22 | 28,760 |
| Sipernat 2200 (non dusty) | 40,430 |
| Limestone | 41,480 |
| Sipernat 22/Limestone 15/85 | 38,680 |
| Sipernat 22/Limestone 30/70 | 38,690 |
| Sipernat 22/Limestone 50/50 | 35,930 |

After the steam challenge, 56% of the xylanase activity could be recovered from a carrier containing Sipemat 22/Limestone 30/70.

Protein degradation of steam treated feed containing protease was investigated by measurement of the nitrogen release from the proteins. After incubation of the feed, the liquid and solid fraction of the extract are separated by centrifugation. The nitrogen content of the liquid fraction is taken as a measure for protein degradation, because (insoluble) proteins are degraded into (soluble) peptides and amino acids. The nitrogen content of the liquid fraction is determined by Kjeldahl analysis.

Xylanase Stabilisation Via the Syrup Process

A trehalose syrup was prepared as described in Example 1. An alpha-amylase was combined with a trehalose syrup and silica gel. The mixture was spray dried and the final product contained between 5% w/w up to 45% w/w of trehalose. The product obtained was heated to 90° C. above a steam bath. The enzyme activity was measured for samples that were heated for 1 and 3 minutes and compared with the control. Trehalose levels of 25% w/w provide >96% of heat stability up to 3 minutes. Formulations containing 5% w/w also provide a significant level of heat stability

TABLE 4

Recovery of alpha-amylase after heating at 90° C. for 0, 1 or 3 minutes

| | Trehalose (% w/w) | | | |
|---|---|---|---|---|
| Time (min) | 5 | 25 | 40 | 45 |
| 0 | 100 | 100 | 100 | 100 |
| 1 | 78 | >100 | >100 | >100 |
| 3 | 87 | 96 | >100 | >100 |

Other Enzymatic Activities

Samples of 80 g were extracted at room temperature in 800 ml phosphate buffer pH 6.0 (0.01 M) for 45 min with continuous stirring on a magnetic stirrer. From the samples for the standard curve, 20 g was extracted in 200 ml phosphate buffer under identical conditions. All extracts were then centrifuged at 3000 rpm (1610×g) for 5 min. Enzyme activities in the supernatant were determined using commercially available enzyme assays.

CONCLUSIONS

Trehalose is a naturally occurring, non-reducing disaccharide, which shows a remarkable chemical interaction with enzymes. A major attribute is the stabilization of enzymes, which can possibly be explained by the reduction of enzyme-water hydrogen bonds and an increase of enzyme-trehalose hydrogen bonds. Trehalose dissolves easily in an aqueous environment and consequently is readily soluble in the gastrointestinal tract.

Two processes were evaluated and a first screening revealed that the syrup process gives the best improvement of the steam-stability for both protease and xylanase encapsulated in trehalose. Heat processing resulting in product temperatures between about 70° C. and about 90° C. for between about 25 seconds and about 150 seconds caused less than a 60% loss in activity of the enzyme so that at least 40% of the starting activity of the enzyme remained. Spray-dried products showed lower recoveries after steam treatment, but the process seems capable of activating the enzymes. Higher activity units were often recovered compared to the units originally added to the formulation. Although spray drying resulted in poorer steam-stability it should be noted that the process itself was performed on an unrefined spray-dryer with limited control of all temperature parameters and that the potential of spray drying still seems significant.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art that have the disclosure before them will be able to make modifications and variations therein without departing from the scope of the invention.

We claim:

1. A stabilized enzyme composition, prepared by a process comprising the steps of:
   (a) preparing a saccharide syrup by dissolving a saccharide in water heated to a temperature of between 50° C. to 100° C. prior to said dissolving in a 1 to 1 up to a 1 to 10 ratio;
   (b) evaporating water from said syrup by further heating such that the residual amount of remaining water is between 20% and 0.01%;
   (c) mixing an enzyme formulation into said syrup immediately following said evaporation wherein said syrup has a temperature between 50° C. and 130° C. and mixture comprises between 99%-10% of said saccharide and between 1%-75% of said enzyme formulation;
   (d) placing said enzyme mixture on a carrier for cooling, wherein the resulting enzyme composition comprises between 5%-65% mixture and between 35%-95% carrier, and wherein said enzyme composition prepared by said process has enhanced thermal stability compared to the same enzyme-containing starting material not stabilized by the process.

2. The stabilized enzyme composition as defined in claim 1, wherein the sugar saccharide is selected from the group consisting of disaccharides and oligosaccharides.

3. The stabilized enzyme composition as defined in claim 2, wherein the disaccharide is selected from the group consisting of sucrose and trehalose.

4. The stabilized enzyme composition as defined in claim 2, wherein the oligosaccharide is selected from the group consisting of melezitose, verbascose, melibiose, sucralose and raffinose.

5. The stabiized enzyme composition as defined in claim 1, wherein the enzyme formulation comprises a hydrolase selected from the group consisting of proteases, xylanases, alpha-amylases, cellulases, β-glucanases, α-galactosidases, beta-mannases, polygalacturonases, arabinases, galactanases, arabinofuranosidases, feroyl esterases and glucosidases.

6. The stabilized enzyme composition as defined in claim 1, wherein said carrier is selected from the group consisting of limestone, vermiculite, silica, cyclodextrin, maltodextrin, gelatin, cornstarch, sepiolite, bentonite, zeolite and cellulose.

7. A method of preparing an enzyme composition having enhanced thermal stability, comprising the steps of:
   (a) heating water to 100° C. to increase the sugar saturation point of said water;
   (b) dissolving trehalose in said heated water in a 1 to 1 up to a 1 to 10 ratio to form a syrup;
   (c) heating the syrup further to remove water from the syrup such that the residual amount of remaining water is between 20% and 0.01%;
   (d) adding an enzyme-containing starting material to the trehalose syrup to create a mixture; and
   (e) creating a dry powder of the enzyme-containing starting material encapsulated in a trehalose from the mixture by a step selected from the group consisting of spray drying the mixture and distributing the mixture on a carrier to produce an enzyme composition having enhanced thermal stability during pelleting over the unprotected enzyme-containing starting material.

8. A method as defined in claim 7, wherein the enzyme-containing starting materials comprise a hydrolase selected from the group consisting of proteases, xylanases, alpha-amylases, celluloses, β-glucanases, α-galactosidases, α-amylase, beta-mannases, polygalacturonases, arabinases, galactanases, arabinofuranosidases, feroyl esterases and glucosidases.

9. A method as defined in claim 7, wherein the dry powder is obtained by spray drying.

10. A method as defined in claim 7, wherein the dry powder is obtained by distributing the mixture on a carrier.

11. A method as defined in claim 10, wherein the carrier is selected from the group consisting of limestone, vermiculite, silica, cyclodextrin, maltodextrin, gelatin, cornstarch, sepiolite, bentonite, zeolite and cellulose.

12. A method as defined in claim 7, wherein the activity of the enzyme composition upon pelleting of the composition at between about 70° C. and about 90° C. for between about 25 seconds and about 10 minutes is at least 40% of the starting activity of the enzyme-containing starting material.

13. A method for preparing an enzyme composition, comprising the steps of:
   (a) adding a non-reducing sugar in a 1 to 1 up to a 1 to 10 ratio with water heated to 100° C.;
   (b) heating the sugar and water further to evaporate part of the water to form a syrup having between 0.01% and 20% residual water;
   (c) adding an enzyme-containing liquid to form a mixture; and
   (d) creating a powder of the enzyme encapsulated in the non-reducing sugar from the mixture by a step selected from the group consisting of spray drying the mixture and distributing the mixture on a carrier to produce an enzyme composition having enhanced thermal stability during pelleting over the unprotected enzyme-containing starting material.

14. The method for preparing an enzyme composition as defined in claim 13, wherein the sugar is selected from the group consisting of disaccharides and oligosaccharides.

15. The method for preparing an enzyme composition as defined in claim 14, wherein the disaccharide is selected from the group consisting of sucrose and trehalose.

16. The method for preparing an enzyme composition as defined in claim 14, wherein the oligosaccharide is selected from the group consisting of melezitose, verbascose, melibiose, sucralose and raffinose.

17. The method for preparing an enzyme composition as defined in claim 13, wherein the enzyme-containing liquid comprises a hydrolase selected from the group consisting of proteases, xylanases, alpha-amylases, cellulases, β-glucanases, α-galactosidases, beta-mannases, polygalacturonases, arabinases, galactanases, arabinofuranosidases, feroyl esterases and glucosidases.

18. The method as defined in claim 13, wherein the activity of the enzyme composition upon pelleting of the composition at between about 70° C. and about 90° C. for between about 25 seconds and about 10 minutes is at least 40% of the starting activity of the enzyme-containing starting material.

* * * * *